(12) United States Patent
Pastorelli

(10) Patent No.: US 7,073,214 B2
(45) Date of Patent: Jul. 11, 2006

(54) SHOWER-BATH BOOTH STRUCTURE

(75) Inventor: Domenico Pastorelli, San Remo (IT)

(73) Assignee: Candido Bruto (IT)

( * ) Notice: Subject to any disclaimer, the term of this patent is extended or adjusted under 35 U.S.C. 154(b) by 47 days.

(21) Appl. No.: 10/343,284

(22) PCT Filed: Dec. 11, 2001

(86) PCT No.: PCT/EP01/15439

§ 371 (c)(1),
(2), (4) Date: Oct. 10, 2003

(87) PCT Pub. No.: WO02/47526

PCT Pub. Date: Jun. 20, 2002

(65) Prior Publication Data

US 2004/0068789 A1    Apr. 15, 2004

(30) Foreign Application Priority Data

Dec. 12, 2000  (IT)  .......................... MI2000A2667

(51) Int. Cl.
*A47K 3/30* (2006.01)

(52) U.S. Cl. .................. 4/597; 4/612; 4/614

(58) Field of Classification Search ............... 4/596, 4/597, 605, 612, 613, 614
See application file for complete search history.

(56) References Cited

U.S. PATENT DOCUMENTS 3,007,178 A * 11/1961 Altman et al. ............ 4/525
4,829,608 A    5/1989 Stevens et al.
5,255,399 A * 10/1993 Park ............................ 4/525

FOREIGN PATENT DOCUMENTS

| DE | 80 30 053 U1 | 5/1981 |
| EP | 0 331 782 A1 | 9/1989 |
| WO | WO-92/17242 A1 | 10/1992 |

* cited by examiner

*Primary Examiner*—Robert M. Fetsuga
(74) *Attorney, Agent, or Firm*—Akerman Senterfitt

(57) ABSTRACT

A shower-bath booth structure (1) comprising up-right elements arranged to define a booth and formed with at least one clear portion, a base element (2) provided with a water drain outlet (9), and a sprinkling device (5) connected to the water supply is described. Advantageously according to the present invention, the shower-bath booth structure (1) further comprises tanning lamps (7) oriented to illuminate the interior of said booth through the clear portion.

13 Claims, 4 Drawing Sheets

SHOWER-BATH BOOTH STRUCTURE

TECHNICAL FIELD

The present invention relates to a booth structure for shower baths.

In particular, the invention relates to a shower-bath booth structure, comprising upright elements arranged to define a booth and formed with at least one clear portion, a base element provided with a water drain outlet, and a sprinkling device connected to the water supply.

BACKGROUND ART

As it is well known, a shower-bath booth structure typically comprises a shallow drained basin, a water sprinkler, and a combination faucet connected to the water supply. All these components are located within a booth that is formed of vertical clear glass or plastics panes, or masonry walls, or combinations thereof. Conventionally, the function of the booth is only to confine the area where a user stands under the water jet.

The shower-bath booths are widely used in domestic application as well in hotels and gyms.

Also known are structures, mostly in the form of cylindrical booths, which are equipped with a set of tanning lamps applied to their walls, the lamps being oriented to illuminate the booth interior area where a user can get "sun" tanned.

The tanning structures, wherein the whole body of the user is illuminated and thus tanned, have a great volume and weight. So, such structures are usually used only in gyms or specialised organisations like aesthetic centres.

Also known are tanning apparatuses to be used in domestic environment, which comprise a set of tanning lamps oriented to illuminate only a restrict area, e.g. the face of the user. Such domestic apparatuses are reduced in volume and weight.

DISCLOSURE OF INVENTION

The present invention is directed to provide a booth structure that one can use to take a shower bath as well as to become sun tanned.

Another object of the present invention is to provide a shower-bath booth structure of simple construction and reliable performance, which can be cost-efficient.

A further object of the p resent invention is to provide a shower-bath booth structure which can be used in domestic application.

These and other objects, that will become clearer hereinafter, are achieved by a shower-bath booth structure comprising upright elements arranged to define a booth and formed with at least one clear portion, a shallow base element provided with a water drain outlet, and a sprinkling device connected to the water supply, said structure being characterised in that it comprises tanning lamps oriented to illuminate the booth interior through said at least one clear portion.

Additional features and advantages of the invention will be apparent from a description of preferred embodiments thereof, given by way of non-limitative examples in relation to the accompanying drawings, in which:

MODES FOR CARRYING OUT THE INVENTION

Figure 1:
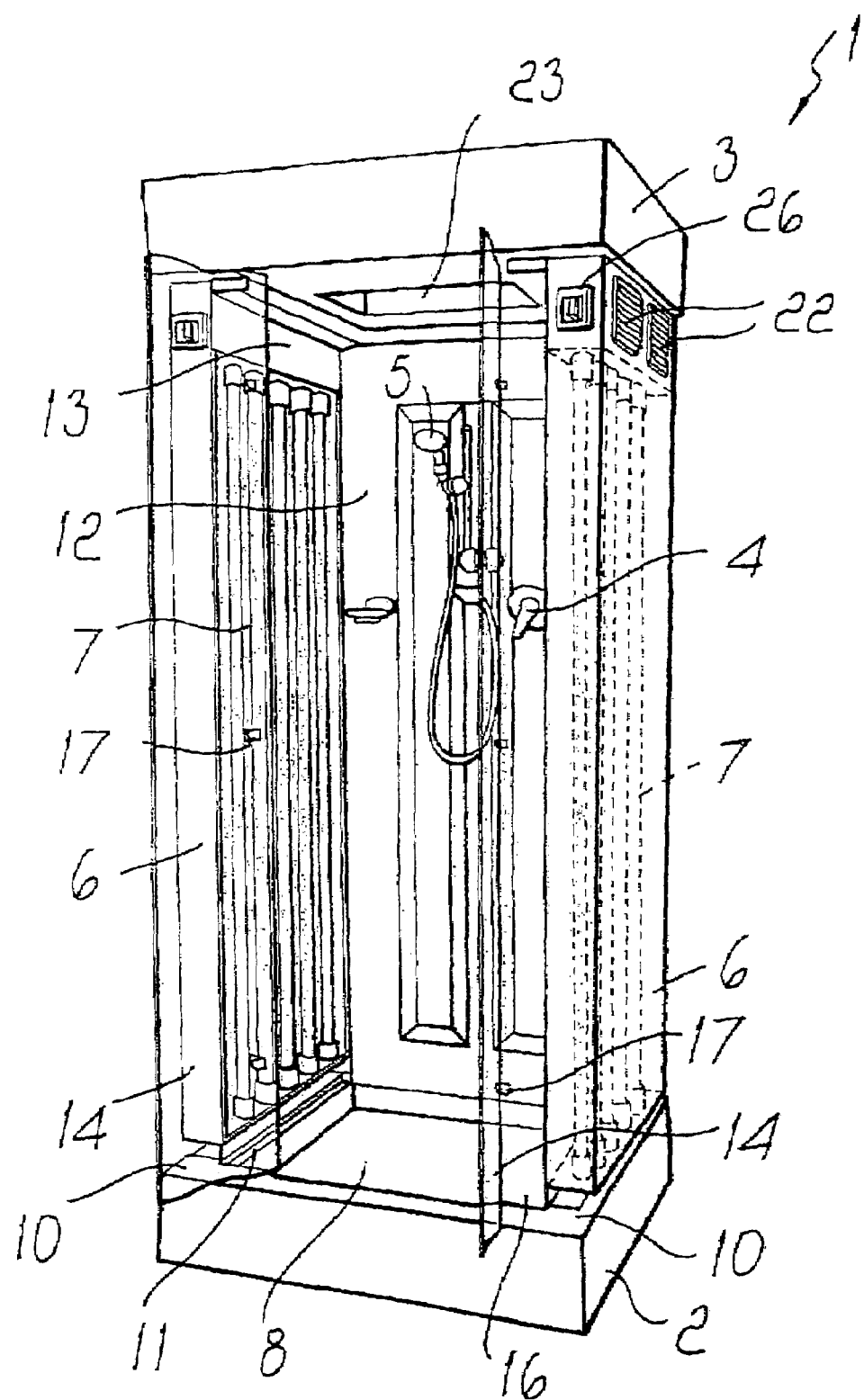
FIG. 1 is a perspective view of a shower-bath booth structure according to the invention.
Figure 2:
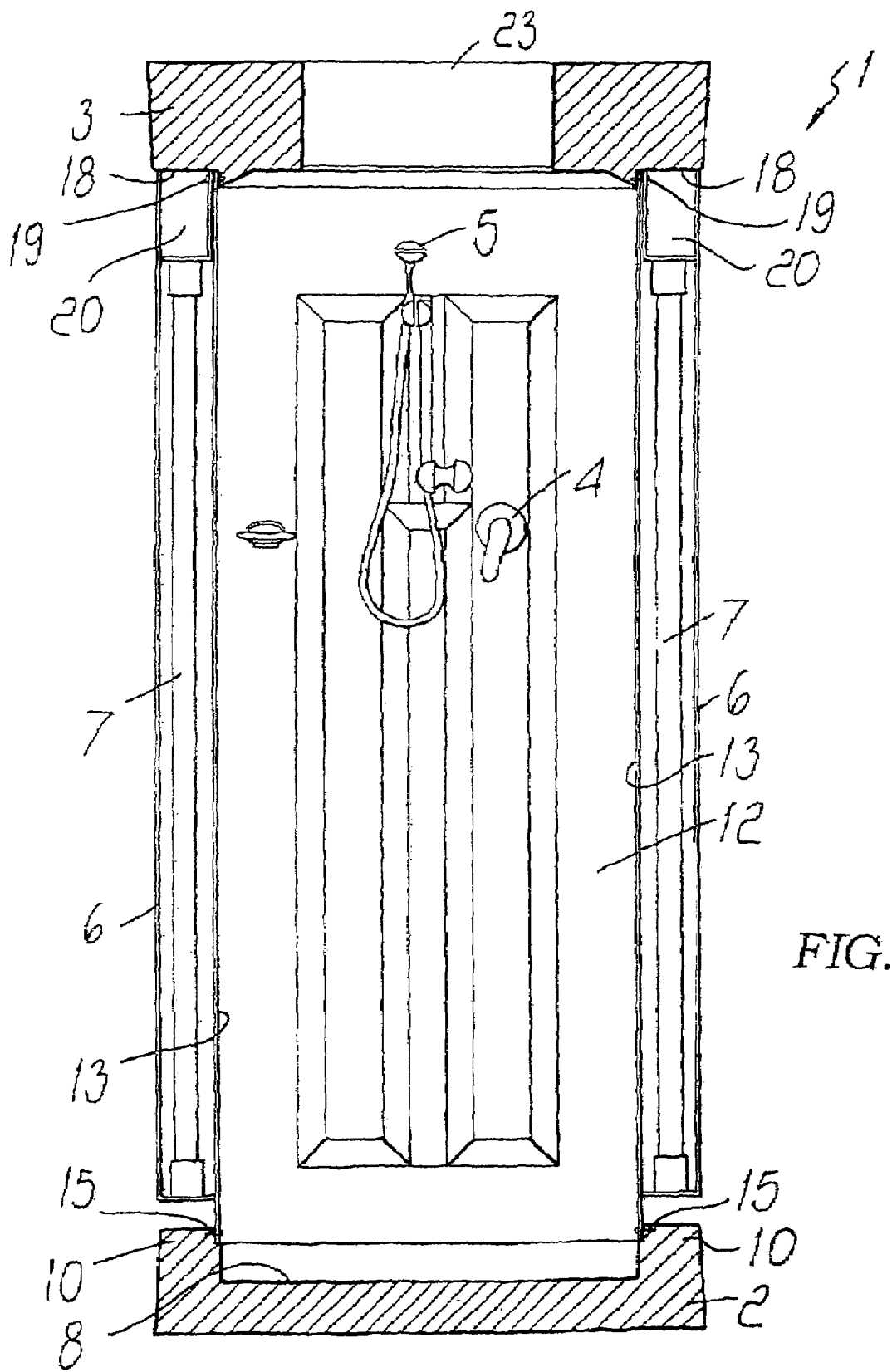
FIG. 2 is a sectional front view of the shower-bath booth structure according to the invention.
Figure 3:
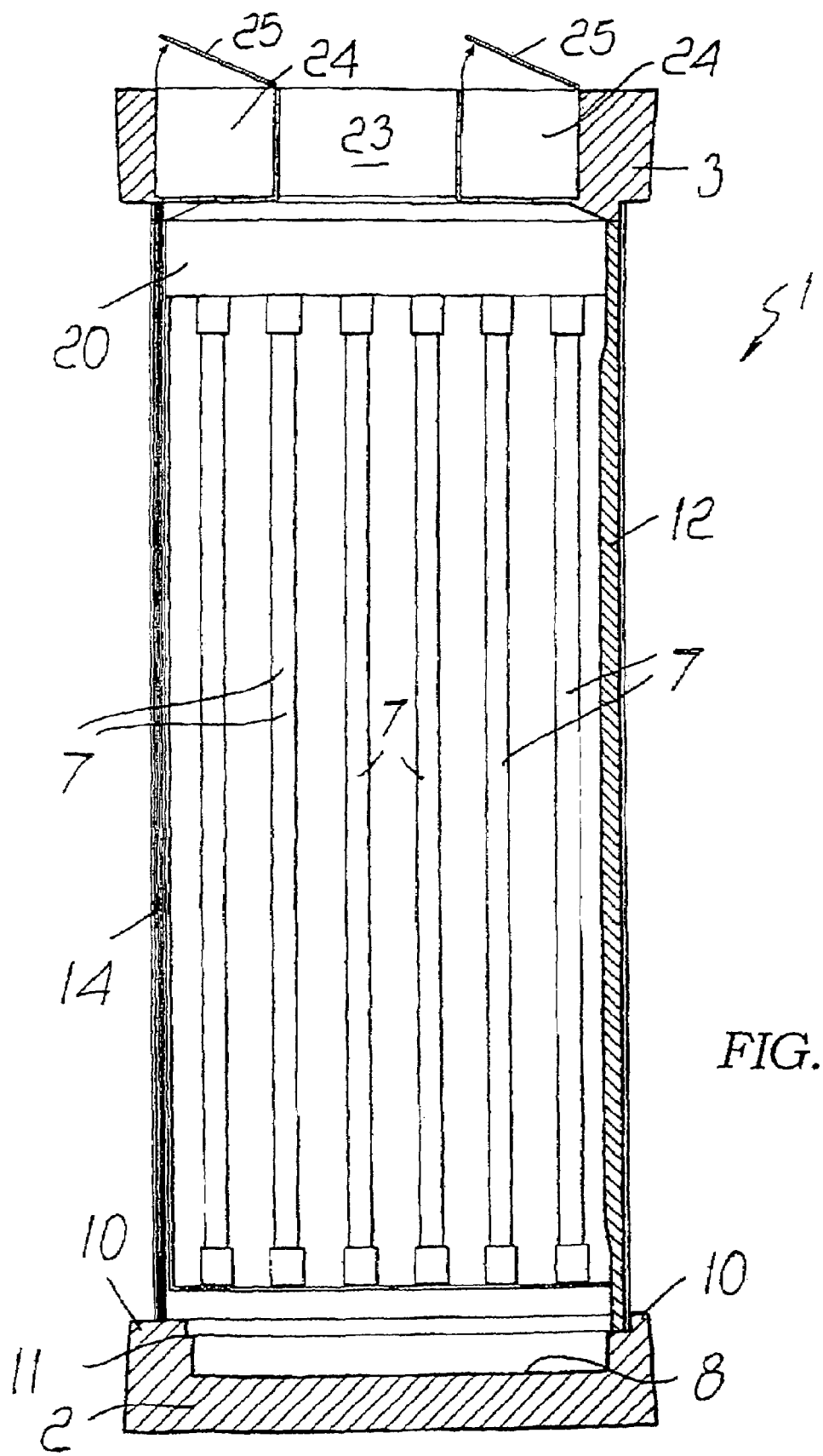
FIG. 3 is a sectional side view of the shower-bath booth structure according to the invention.
Figure 4:
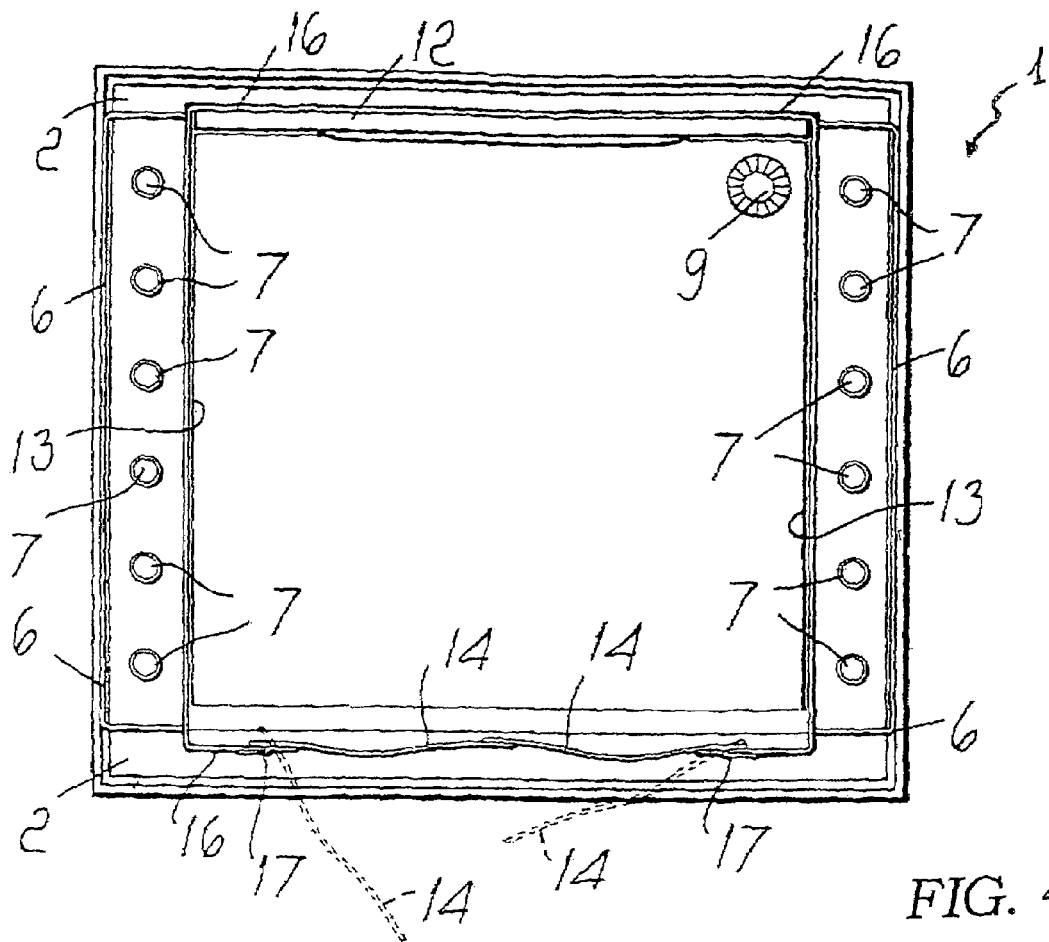
FIG. 4 is a sectional view from above of the shower-bath booth structure according to the invention.
Figure 5:
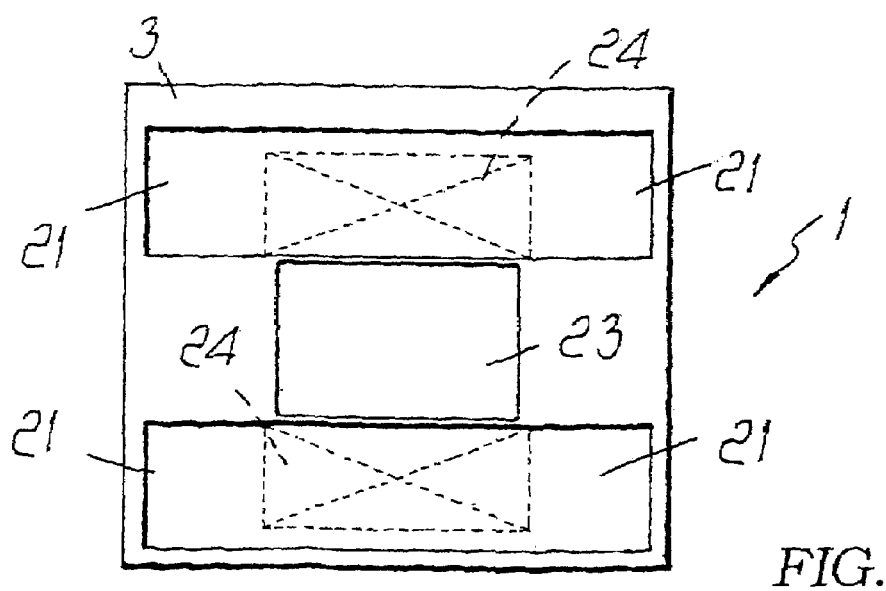
FIG. 5 is a top plan view of the shower-bath booth structure according to the invention.

With reference to the drawings, a shower-bath booth structure is shown generally at 1 and comprises upright elements, which are mounted on a base element 2 and associated at the top with a body 3. According to a preferred embodiment of the invention, the body 3 is box-shaped. However, a cylindrical body can also be used.

The upright elements define a clear shower-bath space that includes a combination faucet 4 and a sprinkling device 5 conventionally connected to the water supply. According to a preferred embodiment of the invention, comprising a box-shaped body 3, such clear shower-bath space has a substantially parallelepipedic shape.

The shower-bath booth structure according to the invention includes support structures 6 for tanning lamps 7 (two in the example shown in the figures), the lamp support structures being so arranged on the upright elements as to allow the tanning lamps 7 to illuminate the booth interior. The lamp support structures 6 also provide support for the roof of the body 3.

The base element 2 is made of reinforced fibres in the form of a shallow basin 8 provided with a water-draining outlet 9, and formed with ledge-shaped edges 10 along which peripheral support steps 11 are defined to receive the upright elements thereon.

Advantageously according to the present invention, the ledge-shaped edges 10 and the corresponding peripheral support steps 11 facilitate the construction of the shower-bath booth structure.

Also provided are a back panel 12 of reinforced fibres supporting the sprinkler 5 and the combination faucet 4, two clear side closing panels 13 advantageously made of Perspex, and clear front swing doors 14.

Each side panel 13 is secured on the peripheral support steps 11 along the edges 10 of the base element 2 by screw fasteners 15, and has longitudinal end edges 16 turned inwards to define the booth corners.

The edges 16 of the side panels 13 overlap the back panel 12 rearwardly, and carry hinges 17 forwardly for allowing mounting and swinging of the doors 14.

The box-shaped element 3 resting on the top ends of the upright panels overhangs the side panels 13, thereby defining an abutment surface 18.

The upper section of a lamp support structure 6 is associated with the surface 18, as by means of screw fasteners 19, to almost fully span the clear panel 13 exterior.

The lamp support structure 6 includes a number of tanning lamp holders that comprise sealed tubes 7 arranged vertically and screen from the water jet by the side panels 28.

Downwardly, the lamp support structure 6 is raised off the ledge-shaped edges 10 of the base element 2 to provide, advantageously, a safe space preventing the lamp support structure 6 from being swept with water.

The upper section of the lamp support structure 6 has a heat dissipating space 20, which is put in communication with the ambient by openings 21 formed through the box-shaped body 3, and has side grids 22 for the purpose of keeping the tanning tubes 7 cooled.

The box-shaped body 3 is also provided centrally with a steam dissipating space 23 for the shower area, and is equipped with electric sockets 24 for connection to the power supply and to electronic control devices controlling the tanning lamps 7, the sockets mounting protective covers 25.

Such protecting covers 25 providing for a reliable performance of the

A user can turn on the lamps by depressing push-button switches 26 located in the upper section of the lamp support structures 6.

It has been found in actual practice that the invention achieves its objects by providing a shower-bath booth structure that doubles as a traditional shower booth, when the sprinkler and faucet are operated, and a solar booth, when the tanning lamps are operated.

Advantageously according to the invention, the water jet of the sprinkler 5 could cool a user when using the tanning lamps, thus enhancing the performance of the shower-bath booth structure from the standpoint of view of the wellness of the users.

A number of changes and modifications may be made unto the device according to the invention within the inventive principle, and any parts thereof may be replaced with technical equivalents.

It is understood that the materials and dimensions employed may be any ones filling the demands and suiting the state of the art.

The invention claimed is:

1. A shower-bath boot structure, comprising:
   upright elements arranged to define a booth and formed with at least one clear portion;
   a base element provided wit a water drain outlet;
   a sprinkling device connected to the water supply; and
   tanning lamps oriented to illuminate the interior of said booth through said at least one clear portion,
   wherein the upright elements include a back panel carrying the sprinkling device, clear side closing panels, and at least a clear front door panel which can be opened, and
   wherein the side closing panels are each secured on said support steps along the raised peripheral edges of the base element by screw fasteners, and have their longitudinal end edges turned inwards to define booth corners, the inward turned edges of the side closing panels overlapping the back panel rearwardly and carrying hinges forwardly for mounting the clear front door panels.

2. A shower-bath booth structure according to claim 1, wherein the base element includes a shallow drained basin having raised peripheral edges with support steps on which the upright elements abut.

3. A shower-bath booth structure according to claim 1, wherein the base element is associated with a box-shaped element and overhangs the side closing panels to define an abutment surface on each side, an upper section of a lamp support structure for supporting the tanning lamps being associated with the abutment surface, as by screw fasteners, and covering the exterior of the side closing panels.

4. A shower-bath booth structure according to claim 3, wherein the lamp support structure includes a plurality of tanning lamp holders in the form of vertically laid sealed tubes, the side closing panels screening the tanning tubes from a water jet of the sprinkling device.

5. A shower-bath booth structure according to claim 3, wherein the lamp support structure has a bottom end off the raised peripheral edges of the base element to define a safe space effective to prevent the lamp support structure from being swept by a water jet of the sprinkling device.

6. A shower-bath booth structure according to claim 3, wherein the lamp support structure is overlaid with a heat dissipating space connected to the ambient by openings formed through the box-shaped body, and includes side grids for keeping the tanning tubes cooled.

7. A shower-bath booth structure according to claim 1, wherein the base element is associated with a box-shaped body which is provided centrally with a steam dissipating space for a shower area, and with sockets for electric connection to power supply and electronic control devices controlling the tanning lamps, the sockets having protective covers.

8. A shower-bath booth structure comprising:
   upright elements arranged to define a booth and formed with at least one clear portion;
   a base element provided with a water drain outlet and having raised peripheral edges with support steps;
   a sprinkling device connected to the water supply; and
   tanning lamps oriented to illuminate the interior of the booth through the at least one clear portion and supported by a lamp support structure,
   wherein the lamp support structure has a bottom end off the raised peripheral edges of the base element to define a safe space effective to prevent the lamp support structure from being swept by a water jet of the sprinkling device,
   wherein the upright elements include a back panel carrying the sprinkling device, clear side closing panels, and at least a clear front door panel which can be opened, and
   wherein the side closing panels are each secured on the support steps along the raised peripheral edges of the base element by screw fasteners, and have their longitudinal end edges turned inwards to define booth corners, the inward turned edges of the side closing panels overlapping the back panel rearwardly and carrying hinges forwardly for mounting the clear front door panels.

9. A shower-bath booth structure according to claim 8, wherein the base element includes a shallow drained basin having raised peripheral edges with support steps on which the upright elements abut.

10. A shower-bath booth structure according to claim 8, wherein the base element is associated with a box-shaped element and overhangs the side closing panels to define abutment surfaces on each side, the upper section of the lamp support structure being associated with the abutment surface, as by screw fasteners, and covering the exterior of the side closing panels.

11. A shower-bath booth structure according to claim 8, wherein the lamp support structure includes a plurality of tanning lamp holders in the form of vertically laid sealed tubes, the side closing panels screening the tanning tubes from a water jet of the sprinkling device.

12. A shower-bath booth structure according to claim 8, wherein the lamp support structure is overlaid with a heat dissipating space connected to the ambient by openings formed through the box-shaped body, and includes side grids for keeping the tanning tubes cooled.

13. A shower-bath booth structure according to claim 8, wherein the base element is associate with a box-shaped body which is provided centrally with a steam dissipating space for a shower area, and with sockets for electric connection to power supply and electronic control devices controlling the tanning lamps, the sockets mounting protective covers.

* * * * *